United States Patent [19]

Hirata et al.

[11] Patent Number: 4,663,450
[45] Date of Patent: May 5, 1987

[54] OPTICALLY ACTIVE CEPHALOSPORIN ANALOGS

[75] Inventors: Tadashi Hirata, Yokohama; Yukio Hashimoto, Yamato; Takehiro Ogasa, Machida; Shigeru Kobayashi, Machida; Akira Sato, Machida; Kiyoshi Sato, Shizuoka; Seigo Takasawa, Hadano, all of Japan

[73] Assignee: Kyowa Hakko Kogyo Co., Ltd., Tokyo, Japan

[21] Appl. No.: 788,660

[22] Filed: Oct. 17, 1985

Related U.S. Application Data

[63] Continuation of Ser. No. 629,755, Jul. 13, 1984, abandoned, which is a continuation of Ser. No. 390,024, Jun. 18, 1982, abandoned, which is a continuation of Ser. No. 200,556, Oct. 24, 1980, abandoned.

[30] Foreign Application Priority Data

Oct. 25, 1979 [JP] Japan .................. 54-136987
Feb. 23, 1980 [JP] Japan .................. 55-22035
Apr. 26, 1980 [JP] Japan .................. 55-55619

[51] Int. Cl.$^4$ .................. C07D 471/04; A61K 31/435
[52] U.S. Cl. .................. 540/205
[58] Field of Search .................. 546/183

[56] References Cited

U.S. PATENT DOCUMENTS 4,218,793 7/1981 Durkheimer .................. 546/183
4,291,164 9/1981 Hirata et al. .................. 546/183

FOREIGN PATENT DOCUMENTS 2740280 3/1978 Fed. Rep. of Germany .
1538240 1/1979 United Kingdom .

*Primary Examiner*—Mark L. Berch
*Attorney, Agent, or Firm*—Fitzpatrick, Cella, Harper & Scinto

[57] ABSTRACT

Optically active cephalosporin analogs of the formula

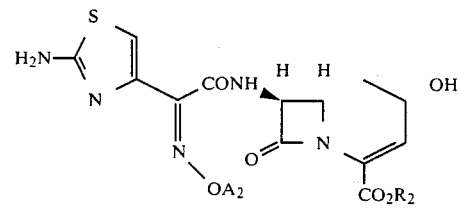

wherein $R_2$ represents a hydrogen or a group represented by the formula

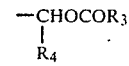

wherein $R_3$ is a straight or branched lower alkyl group having 1 to 6 carbon atoms, a straight or branched lower alkoxy group having 1 to 6 carbon atoms or a phenyl group and $R_4$ is a hydrogen or a straight or branched lower alkyl group having 1 to 6 carbon atoms; and $A_2$ represents a straight or branched lower alkyl group having 1 to 6 carbon atoms or a straight or branched lower alkyl group having 1 to 6 carbon atoms which is substituted with one or two carboxyl groups, are useful as antibacterial agents.

5 Claims, No Drawings

OPTICALLY ACTIVE CEPHALOSPORIN ANALOGS

This application is a continuation of application Ser. No. 629,755 filed July 13, 1984, now abandoned, which is a continuation of application Ser. No. 390,024 filed June 18, 1982, now abandoned, which is, in turn, a continuation of application Ser. No. 200,556, filed Oct. 24, 1980, now abandoned.

BACKGROUND OF THE INVENTION

The present invention relates to optically active cephalosporin analogs and, more particularly, it pertains to optically active compounds of cephalosporin analogs represented by the general formula (I)

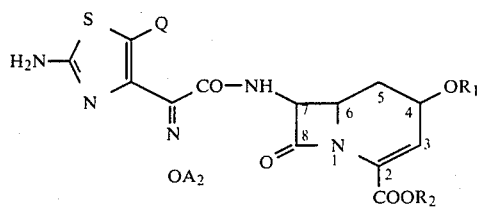

wherein $R_1$ represents a hydrogen, a lower alkyl group or a lower acyl group, $R_2$ represents a hydrogen or a protective group of carboxylic acid, Q represents a hydrogen or a halo group selected from bromo, chloro, fluoro and iodo, $A_2$ represents a hydrogen, a lower alkyl group, a lower alkenyl group, a lower alkinyl group, a cycloalkyl group or an aryl group, those groups being unsubstituted or substituted with suitable substituent(s) which are selected from carboxyl group, cyano group, a halo group, carbamoyl group and a lower alkyloxycarbonyl group, and the hydrogens at the 6- and 7-positions have cis configuration and pharmaceutically acceptable salts thereof.

Heretofore, a carbacephem compound, which is named according to the nomenclature in J. Am. Chem. Soc. 96, 7584 (1974), wherein the sulfur atom of cephalosporin is substituted with a carbon atom and which has a substituted methyl group at the 3-position is described in the above reference and J. Med. Chem. 20, 551 (1977). However, no compound having especially strong antibacterial activity has been reported. In Japanese Published Unexamined Patent Application No. 9296/79 (German Offenlegungsschrift No. 2716707), a carbacephem compound with a 2-aminothiazol-4-yl-2-synmethoxyimino acetamido group but having no substituents at the 4-position is mentioned but neither practical embodiment for preparing the compound nor antibacterial activity thereof is described in the reference.

The present inventors have succeeded in preparing carbacephem compounds having various substituents at the 4-, 5- or 3-position, numbering system of which is as shown in formula (I). The compounds are described in the specifications of Japanese Published Unexamined Patent Application No. 128591/79, G.O. No. 2911786, Japanese Patent Application No. 162008/78 now Japanese Published Unexamined Patent Application No. 87791/80 and U.S. patent application Ser. No. 23,645 filed on Mar. 23, 1979. "G.O." refers to German Offenlegungsschrift hereinafter.

Furthermore, the present inventors have succeeded in preparing novel acylated carbacephems which are new antibiotics having strong antibacterial activities. The compounds are described in the specification of Japanese Published Unexamined Patent Application No. 128591/79, G.O. No. 2911787, U.S. patent application Ser. No. 23,646 and Japanese Patent Application No. 162008/78 now Japanese Published Unexamined Patent Application No. 87791/80.

Among the compounds which are provided by the present inventors and represented by the general formula (II)

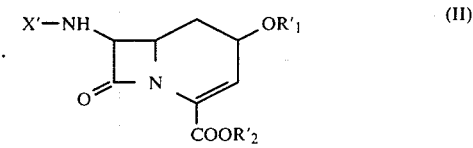

(wherein X' is an acyl group employed in the chemistry of cephalosporins and penicillins, $R'_1$ represents a hydrogen atom, a lower alkyl group or a lower acyl group, and $R'_2$ represents a hydrogen atom or an ester-protecting group conventionally employed in the field of the chemistry of penicillins and cephalosporins, that is, an alkyl group having 1 to 5 carbon atoms such as methyl group, ethyl group, n-propyl group, isopropyl group, n-butyl group, isobutyl group, t-butyl group, etc., a halogenated alkyl group having 1 to 5 carbon atoms such as chloromethyl group, 2,2,2-trichloroethyl group, 2,2,2-trifluoroethyl group, etc., an arylmethyl group having 7 to 20 carbon atoms such as benzyl group, diphenylmethyl group, triphenylmethyl group, etc., an arylmethyl group having 7 to 20 carbon atoms and having methoxy group, nitro group, etc. on the phenyl ring, a substituted silyl group such as trimethylsilyl group or triphenylsilyl group or a group enzymatically or nonenzymatically readily eliminable in vivo, for example, a group represented by the general formula

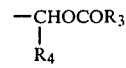

wherein $R_4$ represents a hydrogen atom or a lower alkyl group having 1 to 6 carbon atoms, $R_3$ represents a lower alkyl group having 1 to 6 carbon atoms, a lower alkoxy group having 1 to 6 carbon atoms or phenyl group, etc.), the acyl compound represented by the formula (I')

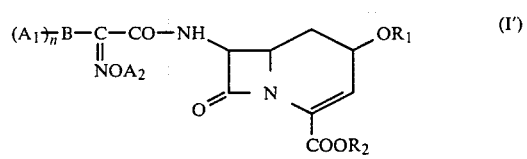

(wherein $R_1$, $R_2$ and $A_2$ have the same meanings as defined above, B represents an unsaturated six membered carbocycle which is selected from cyclohexenyl group, cyclohexadienyl group and phenyl group or a five or six membered heterocycle, $A_1$ represents substituent(s) which is selected from hydrogen atom, hydroxyl group, a lower alkoxy group having 1 to 4 carbon atoms, a halo group, nitro group, amino group, aminoethyl group, methylsulfonamide group and a lower acyloxy group having 1 to 4 carbon atoms, and n is a number of 0 to 5) which has the carbacephem ring represented by the formula (III) (shown below) are reported to have strong antimicrobial activity against Gram-positive and Gram-negative microorganisms in Japanese Patent Application Nos. 122402/78, 133071/78, 162006/78, published respectively as Japanese Published Unexamined Patent Application Nos. 49375/80, 59185/80, 87789/80 and 87790/80, 162007/78 (German Offenlegungsschrift 2911787), etc. Especially the acyl compounds having the carbacephem ring represented by the general formula (I'')

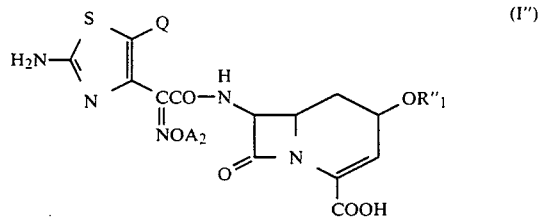

wherein $A_2$ and Q have the same significance as defined above, $R''_1$ represents a hydrogen or a methyl group and $OA_2$ has syn configuration are reported to have strong antimicrobial activity against Gram-positive and Gram-negative microorganisms in the aforementioned patent applications. Hereinafter, compounds represented by the general formula (I), (II), (III), . . . are identified as Compound [I], Compound [II], Compound [III], . . . , respectively.

Since cephalosporin analogs mentioned above are prepared by totally synthetic methods using optically inactive starting materials are reagents, they are optically inactive unless they have a certain optically active acyl group such as D-phenylglycyl group described in the specification of Japanese Patent Application No. 162006/78, now Japanese Published Unexamined Patent Application No. 87789/80, and U.S. patent application Ser. No. 23,646 (German Offenlegungsschrift No. 2911787).

Accordingly, there is a demaned for optically active analogs and methods for production thereof. To this end, it has now been found that certain optically active cephalosporin compounds can be prepared which have unexpectedly increased biological activity.

SUMMARY OF THE INVENTION

In accordance with the present invention optically active acyl compounds represented by the above formula (I) are prepared from optically active compounds of the cephalosporin analogs represented by the general formula (III)

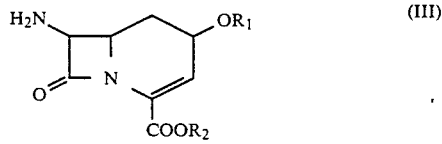

(wherein $R_1$ and $R_2$ have the same significance as defined above and hydrogens at the 6- and 7-positions have cis configuration). The compounds of the present invention have unexpectedly greater antibacterial activity, i.e. 2 to 4 times greater activity against various Gram-positive and Gra-negative microorganisms than the corresponding optically inactive dl-Compound [I].

Optically active Compound [III] and processes for preparing the same are described in U.S. Pat. No. 4,302,540, issued Nov. 24, 1981, of the present inventors which description is expressly incorporated herein by reference.

However, for ease of reference, suitable processes are also set forth hereinafter in Reference Examples 1 and 2.

Optically inactive dl-compounds corresponding to Compound [III] are present as a mixture of equal amounts of optical isomers (III-1) and (III-2) which are mirror images of each other (enantiomers).

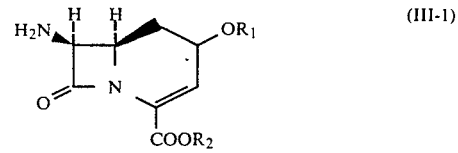

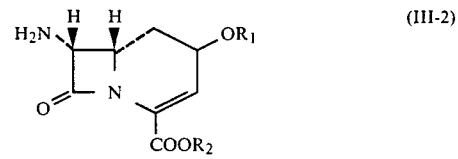

wherein $R_1$ and $R_2$ have the same significance as defined above.

The optically active compounds obtained by the processes in Reference Examples below are assumed to have the absolute structure represented by the general formula (III-1) defined above from various properties, strong antimicrobial activity of the acyl compounds compared with the corresponding optically inactive dl-compound and the relationship between the absolute structure of cephalosporins and activities thereof.

In the following description, the optically active compounds are described as having the absolute configuration of (6R, 7S), i.e. the configuration illustrated by the general formula (III-1) and in the following Examples and Reference Examples, the compounds are named according to the assumed absolute structural formula. It is needless to say that the optically active compounds are more useful as medicines and antimicrobial agents compared with optically inactive compounds and the compounds of the present invention are, therefore, useful as antibacterial agents which may be employed in manners well known in the art.

DETAILED DESCRIPTION OF THE INVENTION

The compounds of the present invention are the optically active compounds of cephalosporin analogs represented by the general formula (I)

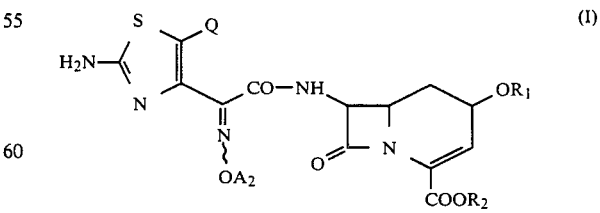

In the formula (I), the definitions of $R_1$, $R_2$, Q and $A_2$ are as follows.

$R_1$ represents a hydrogen, a lower alkyl group having 1 to 5 carbon atoms such as methyl, ethyl, n-propyl, i-propyl, n-butyl, i-butyl, t-butyl, and the like or a lower acyl group represented by R₅CO wherein R₅ is a straight or branched alkyl group having 1 to 5 carbon atoms such as methyl, ethyl, n-propyl, i-propyl, n-butyl, i-butyl, sec-butyl, t-butyl, and the like. Furthermore, it is preferable that the OR₁ group has the same configuration as the hydrogen atoms at the 6- and 7-positions, i.e. 4α-configuration in the structural formula (III-1). However, the compounds having 4β-OR₁ group and the mixed compounds of 4α- and 4β-OR₁ compounds are valuable enough.

R₂ is a hydrogen atom or a protective group of carboxylic acid used in the chemistry of penicillins and cephalosporins.

Suitable R₂ groups are selected from:

straight or branched alkyl groups having 1 to 5 carbon atoms such as methyl, ethyl, n-propyl, i-propyl, n-butyl, i-butyl, t-butyl, and the like;

straight or branched lower alkoxymethyl groups having 1 to 5 carbon atoms such as methoxymethyl, ethoxymethyl, and the like;

straight or branched halogenated alkyl groups having 1 to 5 carbon atoms such as chloromethyl, 2,2,2-trichloromethyl, 2,2,2-trifluoroethyl, and the like;

lower alkylsulfonylethyl groups such as methylsulfonylethyl, ethylsulfonylethyl, and the like;

arylmethyl group having 7 to 12 carbon atoms such as benzyl, diphenylmethyl, trityl, triphenylmethyl, and the like;

substituted silyl groups such as trimethylsilyl, triphenylsilyl, and the like;

substituted arylmethyl groups having 7 to 20 carbon atoms wherein the substituent is methoxy group or nitro group and number of substituents on the phenyl ring is 1 to 5;

protective groups of carboxylic acid represented by the general formula (VI)

wherein R₃ is a straight or branched lower alkyl group having 1 to 6 carbon atoms, a straight or branched lower alkoxy group having 1 to 6 carbon atoms, or a phenyl group, and R₄ is a hydrogen or a straight or branched lower alkyl group having 1 to 6 carbon atoms.

Q represents a hydrogen or a halo group selected from bromo, chloro, fluoro and iodo.

A₂ represents a hydrogen atom, a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or an aryl group, those groups being unsubstituted or substituted with suitable substituent(s) which is selected from carboxyl group, cyano group, a halo group, carbamoyl group and a lower alkyloxycarbonyl group having 1 to 4 carbon atoms.

In general, it is known that thiazolyl group represented by

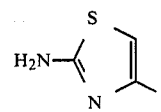

exhibits reversible interconversion with the thiazolinyl group as shown below, and both are usually regarded as identical. In the present specification, both isomers are represented by thiazolyl group. Of course, Compound [I] includes the both isomers based on the reversible interconversion.

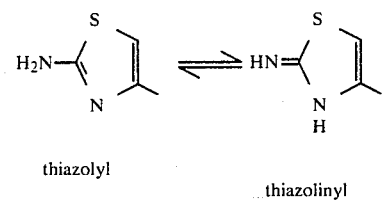

thiazolyl                thiazolinyl

As for OA₂, syn configuration means isomer (A) in the following representation of the stereoisomers.

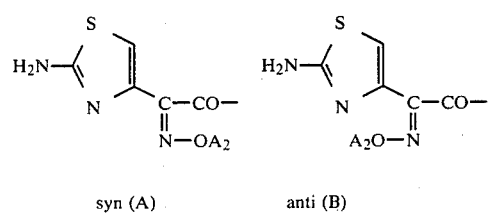

syn (A)              anti (B)

As the pharmaceutically acceptable salts of the compounds of the invention, salts of the inorganic or organic bases, for example, the alkali metal salts such as sodium salts, potassium salts, etc., alkali earth metal salts such as magnesium salts, etc., ammonium salts, trimethylamine salts, triethylamine salts, pyridine salts, procaine salts, purine salts, lysine salts, arginine salts, etc. and salts of inorganic or organic acid, for example, hydrochloride, sulfate, carbonate, phosphate, formate, malate, etc. are exemplified. The pharmaceutically acceptable salts are prepared by the standard methods known in the art.

The compounds of the present invention are produced by acylating an optically active compound represented by the general formula (III-1)

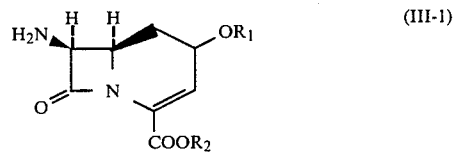

(wherein R₁ and R₂ have the same meanings as defined above) or a functionally equivalent compound with carboxylic acid represented by the general formula (VII)

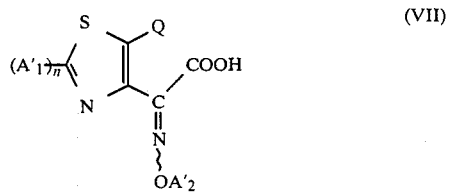

[wherein Q and n have the same significance as defined above, A'₁, represents a substituent which is selected from an amino group and a protected amino group, and A'₂ has the same significance as A₂ in which the carboxy substituent, if any, is protected] or with reactive derivatives of the carboxylic acid and, thereafter, optionally eliminating the protecting group in the group

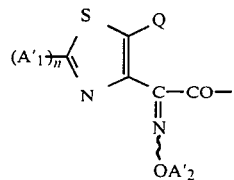

and/or —COOR$_2$ and optionally converting the acylated compounds to pharmaceutically acceptable salts.

A known acylating method is concretely described in Japanese Published Unexamined Patent Application No. 49375/80 and U.S. patent application Ser. No. 23,646 filed on Mar. 23, 1979 (German Offenlegungsschrift No. 2911787).

Isolation and purification of the desired compound are carried out by conventional methods used in organic chemistry.

The invention includes within its scope pharmaceutical compositions comprising, as an active ingredient, Compound [I] or pharmaceuticaly acceptable salt thereof in association with a pharmaceutical carrier or diluent. The compounds of this invention are administered by parenteral (intramuscular, intraperitoneal, intravenous or subcutaneous injection route), oral or rectal route of administration and can be formulated in dosage forms appropriate for each route of adminstration.

Preparations according to this invention for parenteral administration include sterile aqueous or non-aqueous solutions, suspensions and emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying, and dispersing agents. They may be sterilized by filtration through a bacteria-retaining filter, by incorporating sterilizing agents into the compositions, by irradiating the compositions, or by heating the compositions. They can also be manufactured in the form of sterile solid compositions which can be dissolved in sterile water or some other sterile injectable medium immediately before use.

Compositions for oral administration may be presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth and polyvinylpyrrolidone; fillers, for example, lactose, sugar, maize-starch, calcium phosphate, sorbitol and glycine; lubricants, for example, magnesium stearate, talc, polyethylene glycol and silica; disintegrants, for example, potato starch and acceptable wetting agents such as sodium lauryl sulfate.

The tablets may be coated according to methods well known in the art. Oral liquid preparations may be in the form of aqueous or oily suspension, solution, emulsion, syrup, etc. or may be presented as a dry product, for reconstitution with water or other suitable vehicle before use. The liquid preparations may contain conventional additive such as suspending agents, for example, sorbitol syrup, methyl cellulose, glucose sugar syrup, gelatin, hydroxyethylcellulose, carboxymethylcellulose and aluminum stearate gel; emulsifying agents, for example, lecithin and sorbitan monooleate; non-aqueous vehicles which may include edible oils, for example, almond oil and coconut oil, propylene glycol and ethyl alcohol; and preservatives, for example, methyl or propyl n-hydroxybenzoates and sorbic acid.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The dosage is selected depending upon the desired therapeutic effect, the route of administration, and the duration of the treatment. Generally, the present compound is administered to mammalian patients in a dose of 5 to 350 mg/kg of body weight per day to achieve an antibiotic effect.

The present invention is explained by the following Examples.

EXAMPLE 1

Preparation of (4S, 6R, 7S)-7-[2-(2-amino-4-thiazolyl)-2-syn-methoxyiminoacetamido]-4-hydroxy-1-azabicyclo[4,2,0] oct-2-en-8-on-2-carboxylic acid:

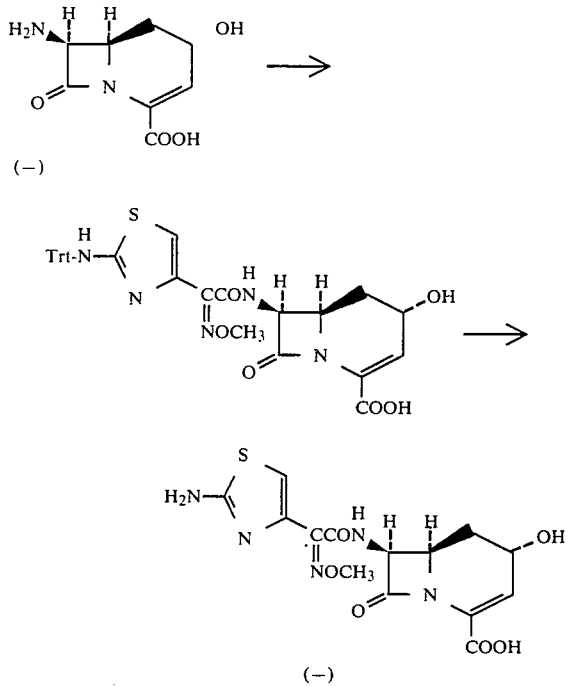

(3-1)

In this Example, 78.8 mg 0.178 m mole) of 2-(2-tritylamino-4-thiazolyl)-2-syn-methoxyiminoacetic acid is dissolved in 0.8 ml of anhydrous dichloromethane and 25 ml (0.178 m mole) of triethylamine is added at a temperature of −20° C. Then, after adding 37 mg (0.178 m mole) of phosphorus pentachloride, the mixture is allowed to react with stirring at a temperature of −20° C. for 40 minutes and concentrated under reduced pressure. The residue is dissolved in 2 ml of anhydrous tetrahydrofuran to make an acid chloride solution.

Separately, 34 mg (0.162 m mole) of the compound obtained as in Reference Example 1-4-(a) is dissolved in a mixture of 1 ml of tetrahydrofuran and 1 ml of water and 79 μl (0.565 m mole) of triethylamine is added. The acid chloride solution prepared above is added dropwise to the solution with stirring under ice cooling and further 20 μl of triethylamine is added. The mixture is allowed to react for two hours and 45 minutes under ice cooling. Then, the mixture is adjusted to a pH of 2.0 with 10% hydrochloric acid and extracted twice with 10 ml of ethyl acetate. The ethyl acetate layers are washed with 10 ml of saturated saline solution, dried with saturated sodium sulfate and concentrated under reduced pressure to obtain 114 mg of a crude acyl compound. The product is dissolved in 10 ml of 50% acetic acid and stirred at a temperature of 50° C. for 30 minutes. The solution is cooled to room temperature and concentrated. The residue is dissolved in 1 ml of methanol. 20 ml of ether and 20 ml of n-hexane are added to the solution and the mixture is subjected to centrifugation to obtain a deposit. The deposit is lyophilized to obtain 51 mg of a solid. The solid is dissolved in a mixture of methanol and water (1:1). The solution is charged on a column packed with 30 ml of HP-20AG and elution is carried out with 40 ml of a mixture of water and methanol 10:1). 30 ml of a mixture of water and methanol (4:1) and 150 ml of a mixture of water and methanol (1:1). Fractions showing an Rf value of 0.3 by silica gel thin layer chromatography [plate: Merck Art. 5719 (product of E. Merck & Co.), solvent:butanol:acetic acid: water=4:1:1] are combined and concentrated under reduced pressure. The concentrate is dissolved in 20 ml of ether and 20 ml of n-hexane to obtain a precipitate. The precipitate is recovered by centrifugation and lyophilized to obtain 29.8 mg (yield 45.5%) as white crystals. Properties of the product are as follows.

IR$\nu_{max}^{KBr}$ (cm$^{-1}$): 3450, 1775, 1635, 1550.

NMR (DMSO d$_6$—CD$_3$OD)δ: 9.28 (1H, J=8.4 Hz), 7.07 (2H, s), 6.75 (1H, s), 6.27 (1H, J=5.4 Hz), 5.56 (2H, m), 2.77−2.04 (2 H, m). The signal of —OCH$_3$ is superimposed with the signals due to the solvent.

$[\alpha]_D^{24°} = -32°$ (c=0.5, methanol).

(1-2)

For further purification, 200 mg of the crystals obtained as in Example 1—1 is dissolved in 1 ml of methanol and 1 ml of hot water is added under heating at 50° C. The solution is allowed to stand at room temperature to obtain white crystals. The crystals obtained by repeating crystallization processes twice is washed with 1 ml of water and dried in vacuo at 45° C. for 12 hours. Yield 120 mg. The product is identified as the desired compound based on the following properties.

Melting point: The product turns purple at about 140° C. and gradually brown and decomposes at 176° to 178° C.

$[\alpha]_D^{19°} = -1°$ (c=0.9, methanol).

NMR (DMSO—d$_6$, 100M)δ: 13.1 (1H, br), 9.25 (1H, d, J=8.3 Hz), 7.20 (2H, br), 6.76 (1H, s), 6.25 (1H, d, J=5.4 Hz), 5.48 (1H, dd, J=8.3, 5.1 Hz), 5.26 (1H, br), 4.30 (1H, m), 3.84 (3H, s), 1.43-2.05 (2H, m), The signal of the proton at the 6-position is superimposed with the signal of —OCH$_3$ (δ3.84).

Elementary analysis. Found C: 43.33%, H: 4.43%, N: 17.89%. Calculated as C$_{14}$H$_{15}$N$_5$O$_6$ S ½ H$_2$O. C: 43.08%, H: 4.13%, N: 17.94%.

High resolutional mass spectrum. The above crystals which are heated at 60° C. for 5 hours in N,O-bistrimethylsilylacetamido are provided as the sample.

Mass=669.23408 (C$_{26}$H$_{47}$O$_6$N$_5$S Si$_4$)

(1-3) Alterative method.

(4S, 6R, 7S)-7-amino-4-hydroxy-1-azabicyclo[4,2,-0]oct-2-en-8-on-2-carboxylic acid obtained as in Reference Example 1-4-b and 1-4-c is treated in the same manner as in Example 1-1 and 1-2, whereby the same desired compound is obtained.

EXAMPLE 2

Antimicrobial activities of the compound obtained in Example 1 are as follows. Heart Infusion Agar Dilution Method (pH 7.2) is used. Cefazolin and the compounds obtained in Reference Examples 3 and 6 are used as a control.

| Microorganism | MIC (μg/ml) | | | |
| --- | --- | --- | --- | --- |
| | A* | B* | C* | Cefazolin |
| Staphylococcus aureus 209-P | 3.12 | 12.5 | 3.12 | 0.02 |
| Staphylococcus aureus Smith | 12.5 | 25 | 25 | 0.78 |
| Staphylococcus epidermidis | 25 | 50 | 12.5 | 0.78 |
| Escherichia coli NIHJC-2 | 0.02 | 0.05 | 6.25 | 1.56 |
| Escherichia coli GN2411-5 | ≦0.01 | 0.02 | 3.12 | 0.78 |
| Escherichia coli Juhl | ≦0.01 | 0.05 | 3.12 | 1.56 |
| Klebsiella pneumoniae 8045 | ≦0.01 | 0.02 | 3.12 | 1.56 |
| Klebsiella pneumoniae Y-60 | ≦0.01 | 0.02 | 6.25 | 3.12 |
| Serratia marcescens T-26 | 0.02 | 0.4 | 100 | >100 |
| Serratia marcescens T-55 | 0.05 | 0.02 | 25 | >100 |
| Proteus mirabilis 1287 | 0.05 | 0.1 | 25 | 12.5 |
| Proteus vulgaris 6897 | ≦0.01 | 0.1 | 25 | 25 |
| Proteus morganii KY 4298 | ≦0.01 | 0.05 | 12.5 | >100 |
| Proteus rettgeri KY 4289 | ≦0.01 | <0.01 | 6.25 | 25 |
| Pseudomonas aeruginosa #1 | 0.73 | 12.5 | >100 | >100 |
| Pseudomonas aeruginosa 145 | 6.25 | 12.5 | >100 | >100 |
| Pseudomonas putida 264 | 0.02 | 0.02 | 12.5 | >100 |

*A: The compound obtained in Example 1-2
B: The compound obtained in Reference Example 3
C: The compound obtained in Reference Example 6

EXAMPLE 3

Preparation of the sodium salt of (4S, 6R, 7S)-7-[2-(2-amino-4-thiazolyl)-2-syn-methoxyiminoacetamido]-4-hydroxy-1-azabicyclo[4,2,0]oct-2-en-8-on-2-carboxylic acid:

In this Example, 131 mg (0.344 m mole) of the crystals obtained as in Example 1 is suspended in 1.5 ml of water. To the mixture is added 28 mg (0.333 m mole) of sodium hydrogencarbonate and the mixture is stirred at room temperature for 4 hours. The obtained soluton is passed through a column packed with 4.5 ml of Diaion HP-20AG and elution is carried out with water. The eluate is collected in 3.3 ml of fractions. Fraction Nos. 20 to 28 are concentrated and the concentrate is again passed through a column packed with 25 ml of Sephadex LH 20. Elution is carried out with water and the eluate is collected in 1.4 ml fractions. Fraction Nos. 12 to 15 are concentrated to obtain crystals which are dried in vacuo at 40° C. for 12 hours. Yield 105 mg (76%). Properties of the product are as follows.

Melting point: The compound turns brown at 165° C. and the color gradually becomes darker.

$[\alpha]_D^{20°}$: $-1°$ (water, c=1.3).

IR(KBr)$\nu_{max}^{cm-1}$: 3400, 1760, 1665, 1600.

NMR (D$_2$O)δ: 6.97 (1H, s), 6.14 (1H, d, J=5.4 Hz), 5.61 (1H, d, J=5.1 Hz), 4.47−4.56 (1H, m), 3.97−4.21 (1H, m), 3.98(3H, s), 1.53−2.20 (2H, m).

Elementary analysis. Found C: 40.15%, H: 3.74%, N: 16.61%. Calculated as C$_{14}$H$_{14}$N$_5$O$_6$S Na C: 39.91%, H: 3.83%, N: 16.62%.

EXAMPLE 4

Preparation of (4S, 6R, 7S)-7-[2-(2-amino-4-thiazolyl)-2-syn-(2-carboxyprop-2-oxyimino) acetamido]-4-hydroxy-1-azabicyclo[4,2,0]oct-2-en-8-on-2-carboxylic acid:

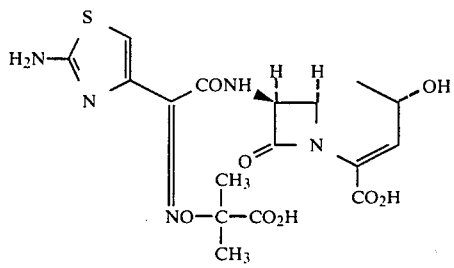

In this Example, 159 mg (0.763 m mole) of phosphorus pentachloride is dissolved in 7.4 ml of anhydrous methylene chloride and the solution is cooled to 0° C. To the solution is added 404 mg (0.706 m mole) of 2-(2-triphenylmethylaminothiazol-4-yl)-2-syn-(2-t-butyloxycarbonylprop-2-oxyimino) acetic acid, followed by stirring at 0° C.for 20 minutes to obtain a pale yellow solution. To the solution is added 0.233 ml (1.67 m mole) of triethylamine and the mixture is stirred at 0° C. for 5 minutes. After the reaction mixture is concentrated under reduced pressure and dried in vacuo, 3.6 ml of anhydrous tetrahydrofuran is added to make an acid chloride solution.

70 mg (0.353 m mole) of (4S, 6R, 7S)-7-amino-4-hydroxy-1-azabicyclo[4,2,0]oct-2-en-8-on-2-carboxylic acid is dissolved in a mixture of 8.4 ml of water and 4.9 ml of tetrahydrofuran and the solution is adjusted to pH 9.8 with triethylamine. The pH of the solution is kept at 3 to 10 with tiethylamine and the above acid chloride solution is added dropwise thereto. The mixture is stirred under ice cooling for one hour and 15 minutes and concentrated under reduced pressure to remove the tetrahydrofuran. The concentrate is adjusted to pH 1 to 2 with 2N aqueous hydrocloric acid, saturated with sodium chloride and extracted with 30 ml of ethyl acetate three times. The ethyl acetate extract is washed with saturated saline solution, dried with anhydrous sodium sulfate and concentrated under reduced pressure to obtain 507 mg of a yellow solid. The concentrate is dried in vacuo and 5 ml of trichloroacetic acid is added. The mixture is allowed to stand at room temperature for 10 minutes. To the mixture is added 3 ml of water and the mixture is again allowed to stand for 10 minutes. The mixture is concentrated under reduced pressure and the resulting yellow slurry is purified by column chromatography using 65 ml of Diaion HP-10 treated with dimethylsulfoxide. Elution is carried out with 65 ml of water, 300 ml of a mixture of water and methanol (10:1) and 420 ml of a mixture of water and methanol (6:1) to obtain fractions 1 to 25, 26 to 60 and 61 to 130, respectively. Fraction Nos. 42 to 95 are combined and concentrated under reduced pressure to obtain 35.3 mg of a crude product. The product is purified by column chromatography using 7 ml of Diaion HP-10. Elution is carried out with 20 ml of water, 40 ml of a mixture of water and methanol (20:1), 40 ml of a mixture of water and methanol (15:1) and 100 ml of a mixture of water and methanol (10:1) to obtain fractions 1 to 15, 16 to 43, 44 to 70 and 71 to 136, respectively. Fraction Nos. 26 to 90 are combined and concentrated under reduced pressure to obtain 22.1 mg (13.8%) of the desired product. Properties of the product are as follows.

IR$\nu_{max}^{cm-1}$ (KBr): 1770, 1660, 1635.

NMR (DMSO-d$_6$)δ: 9.28 (1H, d, J=8.3 Hz), 7.26(3H, s), 6.73(1H, s), 6.33(1H, d, J=4.9 Hz), 5.53(1H, dd, J=5.0, 8.3 Hz), 5.3–5.4 (1H, m), 4.3–4.4 (1H, br), 3.8–4.0(1H, m), 1.6–2.0 (2H, m), 1.41(6H, s)

$[\alpha]_D^{24°} = -24.4°$ (methanol, c=1.0)

EXAMPLE 5

Preparation of (4S, 6R, 7S)-7-[2-(2-amino-5-bromo-4-thiazolyl)-2-syn-methoxyiminoacetamido]-4-hydroxy-1-azabicyclo[4,2,0]oct-2-en-8-on-2-carboxylic acid:

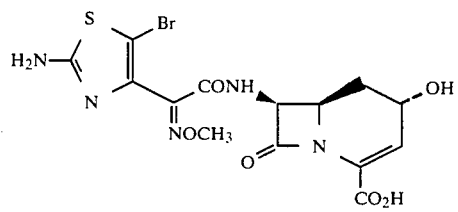

In this Example, 170 mg (0.356 m mole) of 2-(2-tritylamino-5-bromo-4-thiazolyl)-2-syn-methoxyiminoacetic acid is dissolved in 2 ml of anhydrous tetrahydrofuran and 49 μl (0.356 m mole) of triethylamine is added at −20° C. After adding 74 mg of phosphorus pentachloride, the mixture is allowed to react with stirring at −20° C. for one hour.

Separately 32 mg (0.162 m mole) of (4S, 6R, 7S)-7-amino-4-hydroxy-1-azabicyclo[4,2,0]oct-2-en-8-on-2-carboxylic acid is dissolved in a mixture of 2 ml of tetrahydrofuran and 2 ml of water and 71 μl (0.518 m mole) of triethylamine is added. The acid chloride solution prepared above is added dropwise to the solution with stirring under ice cooling. The mixture is allowed to react for two hours under ice cooling. Then, the mixture is adjusted to pH 2.0 with 1N hydrochloric acid and extracted twice with 10 ml of ethyl acetate. The organic layers are washed with 20 ml of saturated saline solution, dried over sodium sulfate and concentrated under reduced pressure. The residue is dissolved in 10 ml of 50% aqueous acetic acid and stirred at 50° C. for 30 minutes. After concentrating, the residue is dissolved in 10 ml of water and the solution is washed with 10 ml of ethyl acetate. After adjusting the pH to 2 with 1N hydrochloric acid, the aqueous layer is charged on a column packed with 20 ml of Diaion HP-10 and elution is carried out with a mixture of water and methanol (4:1 to 2:1). Fractions showing an Rf value of 0.45 by silica gel thin layer chromatography (solvent:butanol:acetic acid:water=4:1:1) are combined and concentrated under reduced pressure to give 34.2 mg of a white powder (yield 46%). Properties of the product are as follows:

IR $\nu$max(KBr) cm$^{-1}$: 1780, 1770, 1670, 1630, 1540.

NMR(CD$_3$OD)δ: 6.44(1H, d, J=5.4 Hz), 5.59 (1H, d, J=5.1 Hz), 4.4(1H, m), 4.1 (1H, m), 3.98(3H, s), 2.8–1.8(2H, m)

$[\alpha]_D^{24°} = -35.6°$ (c=0.5, methanol)

EXAMPLE 6

Antimicrobial activities of the compound obtained in Example 4 and 5 are as follows. Heart Infusion Agar Dilution Method (pH 7.2) is used. Cefazolin is used as a control.

| Microorganism | MIC (μ/ml) | | |
|---|---|---|---|
| | The compound in Example 4 | The compound in Example 5 | Cefazolin |
| Staphylococcus aureus 209-P | >100 | 50 | 0.05 |
| Staphylococcus aureus Smith | >100 | 50 | 0.2 |
| Staphylococcus epidermidis | >100 | 100 | 0.78 |
| Escherichia coli NIHJC-2 | 0.78 | 3.12 | 1.56 |
| Escherichia coli GN2411-5 | 0.2 | 0.78 | 0.78 |
| Escherichia coli Juhl | 0.4 | 3.12 | 1.56 |
| Klebsiella pneumoniae 8045 | 0.2 | 0.78 | 1.56 |
| Klebsiella pneumoniae Y-60 | 0.2 | 1.56 | 3.12 |
| Serratia marcescens T-26 | 0.78 | 6.25 | >100 |
| Serratia marcescens T-55 | 0.4 | 6.25 | >100 |
| Proteus mirabilis 1287 | 0.02 | 1.56 | 12.5 |
| Proteus vulgaris 6897 | ≦0.01 | 0.2 | 50 |
| Proteus morganii KY 4298 | 0.1 | 1.56 | >100 |
| Proteus retteri KY 4289 | ≦0.01 | ≦0.01 | 12.5 |
| Pseudomonas aeruginosa #1 | 0.78 | 6.25 | >100 |
| Pseudomonas aeruginosa 145 | 3.12 | 25 | >100 |
| Pseudomonas putida 264 | ≦0.01 | 0.2 | 50 |

REFERENCE EXAMPLE 1

Preparation of (4S,6R,7S)-7-amino-4-hydroxy-1-azabicyclo[4,2,0]oct-2-en-8-on-2-carboxylic acid:

1-1. Preparation of disrupted cell suspension.

(1) Cultivation of a microorganism having an ability of optically selective deacylation.

As the seed strain, *Kluyvera citrophila* ATCC 21285 [Biological properties are described in J. General Applied Microbiology 3, 28–31 (1957)] is used.

As the seed medium, an aqueous solution containing 1% polypeptone, 1% yeast extract, 0.5% meat extract, 0.5% sodium glutamate and 0.25% sodium chloride and adjusted at a pH of 7.0 with 5N-NaOH is used. One loopful of the seed strain is inoculated into 10 ml of the seed medium in a large test tube (50 ml) and culturing is carried out at a temperature of 30° C. for 24 hours. The whole of the seed broth is inoculated into 300 ml of the culture medium in 2 l of an Erlenmeyer flask and culturing is carried out with shaking at a temperature of 30° C. The composition of the culture medium is the same as that of the seed medium.

(2) Preparation of disrupted cell suspension.

After culturing for 24 hours, the culture broth is subjected to centrifugation to obtain cell bodies. The cells are washed twice with 50 ml of 0.9% saline solution and suspended in a concentration of 40 mg/ml by dry weight in 1/30M phosphate buffer solution (ph 8.0).

1-2. Preparation of a substrate solution.

In this step, 200 mg of (±)-cis-7β-phenylacetamido-4α-hydroxy-1-azabicyclo[4,2,0]oct-2-en-8-on-2-carboxylic acid obtained as in Reference Example 4 below is added into 9 ml of 1/30M phosphate buffer (pH 8.0). Since the compound is not dissolved, 2N—NaOH is added in a small portion and the mixture is again adjusted at a pH of 8.0 to dissolve the compound. Finally, deionized water is added to make 10 ml of a solution.

1-3. Enzyme reaction.

In this step, 10 ml of the disrupted cell suspension mentioned above is added in 10 ml of the substrate solution and enzyme reaction is carried out at a temperature of 40° C. for 80 minutes. Time course of the reaction is illustrated in Table 1.

TABLE 1

| Reaction period (minutes) | The amount of Compound [I-1]* produced (mg/ml) | Yield (Mol ratio, %) |
|---|---|---|
| 10 | 0.8 | 12.5 |
| 20 | 1.3 | 20 |
| 40 | 1.8 | 29 |
| 60 | 2.1 | 33 |
| 80 | 2.2 | 35 |

*Compound (I-1) wherein $R_1$ is H and $R_2$ is H.

1-4. Isolation and Purification of the desired compound.

(a) After the completion of the reaction, cells are removed by centrifugation from the reaction solution. The supernatant is concentrated under reduced pressure and charged on a column (diameter: 0.88 cm, height: 70 cm) packed with 43 ml of Diaion HP-20AG (100–200 mesh, product of Mitsubushi Kasei Kogyo Co., Ltd.). Elution is carried out with deionized water and the desired compound is eluted from 36 ml to 45 ml of the eluate. The eluate are concentrated under reduced pressure and subjected to high speed liquid chromatography using TRI ROTAR (product of Nippon Bunko Co., Ltd.) and Shodex OH Pak B-804 (product of Showa Denko Co., Ltd.). Elution is carried out with water. Eluates are concentrated under reduced pressure and lyophilized to obtain 37.6 mg of a white powder.

Properties of the product are as follows.

$IR\nu_{max}^{KBr}$ (cm$^{-1}$): 3530, 3190, 1746, 1620, 1550

NMR (D$_2$O, with DSS as an internal standard)δ: 6.17(1H, d, J=5.4 Hz), 4.95(1H, d, J=5.4 Hz), 4.59(1H, m), 4.11(1H, m), 2.23(1H, m), 1.80(1H, m)

The properties of the product coincide well with those of the corresponding dl-compound. The value of optical rotation is $[\alpha]_D^{30°} = +24.2°$ (c=0.153, H$_2$O).

It is assumed that the product is a mixture of the desired compound obtained by purifying as in Methods (b) and (c) and a trace amount of a dextrorotatory compound.

The compound shows a ninhydrin positive single spot at an Rf value of 0.38 on silica gel thin layer chromatography [thin layer plate Merck Art 5721 (product of E. Merck & Co.), solvent for development, ethanol:acetic acid:water=4:1:1]. The Rf value coincides with that of the optically inactive dl-compound.

(b) After the completion of the enzyme reaction carried out as in Reference Example 1-1 to 1-3, cell bodies are removed from the reaction solution by centrifugation and the supernatant is concentrated under reduced pressure. The concentrate is charged on a column (diameter: 0.88 cm, height: 70 cm) packed with 43 ml of Diaion HP-20AG (product of Mitsubishi Kasei Kogyo Co., Ltd., 100–200 mesh). Elution is carried out with water. Eluted fractions (36 ml to 45 ml) containing the desired compound are again concentrated under reduced pressure. The concentrate is charged on a column (diameter: 0.88 cm, height: 33 cm) packed with 20 ml of Diaion WA-30-S (product of Mitsubishi Kasei Kogyo Co., Ltd.) which is in advance made acetic acid form by passing 40 ml of 0.5N aqueous acetic acid through the column. After 20 ml of water is passed through the column to eliminate contaminants such as inorganic ions, 0.5N aqueous acetic acid is passed through it. The desired product is eluted in the fractions (30 to 45 ml) of 0.5N aqueous acetic acid. The fractions are lyophilized to obtain 32 mg of the desired product as pale yellow powder. Properties of the product are as follows and the product is identified as the acetate of the desired compound.

IR$\nu_{max}^{KBR}$ (cm$^{-1}$): 3400, 1805, 1760, 1745(sh), 1600, 1560(sh), 1410.

NMR (D$_2$O, with DSS as an internal standard)δ(ppm): 6.16(1H, d, J=5.4 Hz), 4.89(1H, d, J=5.4 Hz), 4.57 (m, superimposed with the signal due to H$_2$O), 4.08(1H, m), 2.21(1H, m), 1.97(3H, s), 1.78(1H, m).

Optical rotation. $[\alpha]_D^{20°} = -62.1°$ (c=0.16, 1M phosphate buffer, pH 7.0).

(c) Preparation of (4S, 6R, 7S)-7-amino-4-hydroxy-1-azabicyclo[4,2,0]oct-2-en-8-on-2-carboxylic acid (Alternative method):

(c-1) Preparation of (4S, 6R, 7S)-7-t-butoxycarbonyl amino-4-hydroxy-1-azabicyclo[4,2,0]oct-2-en-8-on-2-carboxylic acid:

After the completion of the enzyme reaction carried out as in Reference Example 1-1 to 1-3, cell bodies are removed from the reaction solution by centrifugation and the supernatant is concentrated under reduced pressure. The concentrate is charged on a column (diameter: 0.88 cm, height: 70 cm) packed with 43 ml of Diaion HP-20 (product of Mitsubishi Kasei Kogyo Co., Ltd., 100-200 mesh). Elution is carried out with water. Eluted fractions (36 ml to 45 ml) are combined, concentrated under reduced pressure and lyophilized to obtain 100 mg of a white powder. To the powder are added 1.0 ml of dioxane, 1.0 ml of water, 21 μl of triethylamine and 40 mg of S-t-butoxycarbonyl-4,6-dimethyl-2-mercaptopyridine and the mixture is stirred at room temperature for 4 days and at 40° C. for 17 hours. The reaction solution is concentrated under reduced pressure to reduce the volume to about half. The residue is washed with ethyl acetate three times and the pH of the water layer is adjusted to about 3 with 10% aqueous citric acid under ice cooling. After extracting with ethyl acetate five times, the ethyl acetate layer is washed with saturated saline solution twice, dried with anhydrous sodium sulfate and concentrated under reduced pressure to obtain 6.5 mg of white crystals. The product is identified as the desired compound based on the following properties.

IR$\nu_{max}^{KBr}$ (cm$^{-1}$): 3450, 3350, 1785, 1765, 1640, 1540.

NMR (CD$_3$OD)δ(ppm): 6.42(1H, d, J=5.4 Hz), 5.27(1H, d, J=5.4 Hz), 4.41(1H, m), 3.95(1H, m), 2.3-1.2(2H, m), 1.46(9H, s).

Optical rotation. $[\alpha]_D^{21°} = -38.2°$ (c=0.11, CH$_3$OH).

(c-2) Preparation of (4S, 6R, 7S)-7-amino-4-hydroxy-1-azabicyclo[4,2,0]oct-2-en-8-on-2-carboxylic acid:

In this process, 3 ml of anhydrous methylene chloride is added to 63 mg of (4S, 6R, 7S)-7-t-butoxycarbonylamino-4-hydroxy-1-azabicyclo[4,2,0]oct-2-en-8-on-2-carboxylic acid obtained as in step (c-1) and 3 ml of trifluorocetic acid is added with stirring under ice cooling. The mixture is stirred at the same temperature as above for 3.5 hours. Thereafter, the reaction solution is concentrated under reduced pressure to obtain a brown oily product. The product is treated with ethyl ether to obtain 35 mg of a crude desired product as a yellow powder. The product is charged on a column packed with 50 ml of Diaion HP-20AG (product of Mitsubishi Kasei Kogyo Co., Ltd.) and elution is carried out with water. Fractions positive to ninhydrin color reaction are combined and concentrated under reduced pressure to obtain 31 mg (47.0%) of the trifluoroacetate of the desired compound. The product is identified as the trifluoroacetate of the desired compound based on the following properties.

IR$\nu_{max}^{KBr}$ (cm$^{-1}$): 3400, 1800, 1780, 1680, 1620.

NMR (D$_2$O)δ(ppm): 6.31(1H, d, J=5.4 Hz), 5.00(1H, d, J=54 Hz), 4.60(1H, m), 4.16(1H, m), 2.37-1.66(2H, m).

Optical rotation. $[\alpha]_D^{21°} = -61.9°$ (c=0.0743, H$_2$O).

The compounds obtained in steps (b) and (c) behave exactly same as the compound in step (a) in thin layer chromatography under the same conditions.

REFERENCE EXAMPLE 2

Preparation of (4S, 6R, 7S)-7-amino-4-hydroxy-1-azabicyclo[4,2,0]oct-2-en-8-on-2-carboxylic acid (Alternative method):

(2-1) Preparation of immobilized enzyme.

Cell bodies of Kluyvera citrophila ATCC 21285 cultivated in five 2 l-flasks as in Example 1-1 are suspended in 1/30M phosphate buffer (pH 7.0) in a concentration of 40 mg/ml as dry weight. The cells are subjected to ultrasonic disintegration at 200 W for 2 minutes using ultrasonic disintegrator Model UR.200P (product of Tomy Seiko Co., Ltd.). The disrupted cells are subjected to centrifugation to obtain a supernatant. After adding 1% (weight) of the sulfate of streptomycin, the supernatant solution is allowed to stand overnight. Nucleic acid is removed from the solution and ammonium sulfate is added in a concentration of 70% saturation to deposit enzyme proteins. The deposit is recovered by centrifugation and again dissolved in 50 ml of deionized water. The solution is subjected to dialysis for desalting. The enzyme solution is concentrated under reduced pressure to 10 ml and 0.5 ml of 1M acetic acid-sodium acetate buffer (pH 5) is added. Separately 10 ml of Diaion WK-10 (product of Mitsubishi Kasei Kogyo Co., Ltd.) is pretreated in 1/20M acetic acid-sodium acetate buffer (pH 5). The enzyme solution and WK-10 are mixed and the mixture is stirred at a temperature of 30° C. overnight. Thus, an immobilized enzyme is prepared.

(2-2) Reaction, isolation and purification of the desired compound.

The immobilized enzyme (10 ml) mentioned above and 10 ml of a substrate solution prepared as in Reference Example 1-2 are mixed in a large tube and stirred at a temperature of 40° C. for 2 hours. Reaction solution is subjected to decantation and purification as in Reference Example 1-4. The product obtained shows almost same properties as those in Reference Example 1.

REFERENCE EXAMPLE 3

Preparation of (±)-cis-7β-[2-(2-amino-4-thiazolyl)-2-syn-methoxyiminoacetamide]-4α-hydroxy-1-azabicyclo[4,2,0]oct-2-en-8-on-2-carboxylic acid

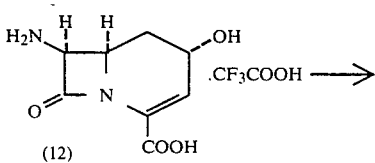

17

-continued

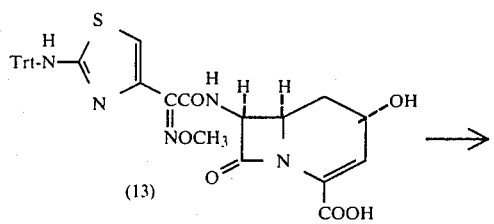

(13)

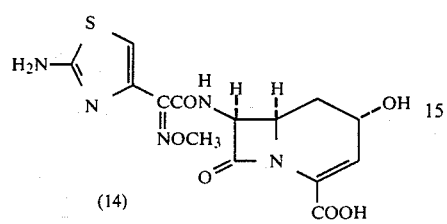

(14)

In this Example, 60 mg (0.203 m mole) of the trifluoroacetate of (±)-cis-(7β-amino-4α-hydroxy-1-azabicyclo[4,2,0]oct-2-en-8-on-2-carboxylic acid obtained as in the method described in Japanese Published Unexamined Patent Application No. 128591/79 is dissolved in a mixture of 1 ml of water and 1 ml of tetrahydrofuran and 56 μl of triethylamine is added to the solution. The mixture is identified as Reaction solution A. On the other hand, 125.7 mg (0.230 m mole) of 2-(2-tritylamino-4-thiazolyl)-2-syn-methoxyiminoacetic acid is dissolved in 1.2 ml of anhydrous methylenechloride and the solution is allowed to react under cooling on a dry-ice-carbon tetrachloride with stirring for 50 minutes after the addition of 39.3 μl of triethylamine and 55 mg (0.264 m mole) of phosphorous pentachloride. The reaction solution is concentrated under reduced pressure and to the residue 1 ml of anhydrous tetrahydrofuran is added to make an acid chloride solution. The acid chloride solution and 28 μl of triethylamine are added to Reaction solution A obtained above in three portions in 5 minutes. The mixture is allowed to react additionally for 35 minutes and adjusted to pH 2.5 with 10% citric acid. The solution is saturated with sodium chloride and extracted with ethyl acetate three times. The organic solvent layers are washed with saturated saline solution and dried with anhydrous sodium sulfate. After filtration and concentration, the residue is subjected to purification by silica gel chromatography (silica gel 15 g, solvent, methanol:chloroform=1:3) to obtain 185.5 mg of a crude acyl product. To 86 mg of the acyl product [Compound (13)] 3 ml of 50% acetic acid is added and the mixture is stirred at a temperature of 50° C. for 50 minutes. The mixture is cooled and the deposited triphenylcarbinol is removed by filtration. The filtrate is concentrated under reduced pressure to obtain a yellow glassy crude product. The product is subjected to purification using 8 ml of Diaion HP-20 (product of Mitsubishi Kasei Kogyo Co., Ltd.) and a solvent of methanol and water (1:9 to 2:1) to obtain 14.5 mg (44.3%) of the desired compound. Properties of the compound are as follows.

IR$\nu_{max}^{KBr}$ (cm$^{-1}$): 3450, 1775, 1670, 1635, 1650.

NMR (DMSO d$_6$-CD$_5$OD)δ: 9.28 (1H, d, J=8.4 Hz), 7.07(2H, s), 6.75 (1H, s), 6.27(1H, d, J=5.4 Hz), 5.56(2H, m), 2.77−2.04(2H, m).

The signal of —OCH$_3$ is superimposed with the signals due to the solvent.

18

REFERENCE EXAMPLE 4

Preparation of (±)-cis-7β-phenylacetamide-4α-hydroxy-1-azabicyclo[4,2,0]oct-2-en-8-on-2-carboxylic acid

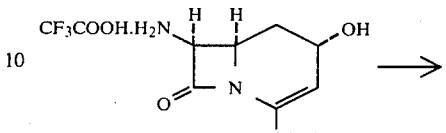

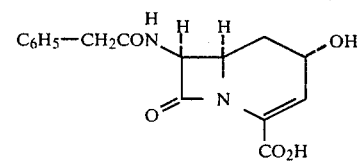

In this Example, 194.6 mg (0.623 m mole) of the trifluoroacetate of (±)-cis-7β-amino-4α-hydroxy-1-azabicyclo-[4,2,0]oct-2-en-8-on-2-carboxylic acid is dissolved in a mixture of 3.1 ml of water and 6.2 ml of acetone and 209 mg (2.49 m mole) of sodium hydrogencarbonate are added to the solution. Then, 12.5 mg (0.810 m mole) of phenylacetylchloride in 2 ml of acetone is added dropwise to the mixture with stirring under ice cooling. 10.5 mg (0.068 m mole) and 17.6 mg (0.114 m mole) of phenylacetylchloride are added to the mixture after 1.5 and 2.5 hours, respectively. After 2 hours and 45 minutes, the reaction is concentrated under reduced pressure to remove acetone. Water (10 ml) and 1N hydrochloric acid (1 ml) are added to the concentrate and the resulting solution is extracted three times with 20 ml of ethyl acetate. The ethyl acetate layer is washed with saturated saline solution, dried with anhydrous sodium sulfate, subjected to filtration and concentrated under reduced pressure.

The obtained brown oily product is triculated with ether, subjected to filtration and dried to obtain 120 mg (60.4%) of a powder of the desired compound. Properties of the product are as follows.

IR$\nu_{max}^{KBr}$ (cm$^{-1}$): 3400, 1780, 1670, 1640.

NMR (CD$_3$OD)δ: 7.27(5H, s), 6.39(1H, d, J=5.4 Hz), 5.46(1H, d, J=5.1 Hz), 4.37(1H, m), 4.01(1H, m), 3.57(2H, s), 2.0-1.1(2H, m).

REFERENCE EXAMPLE 5

Preparation of (±)-cis-7β-[(R)-2-t-butyloxycarbonylamino-2-phenylacetamido]-4α-hydroxy-1-azabicyclo[4,2,0]oct-2-en-8-on-carboxylic acid, t-butyl ester

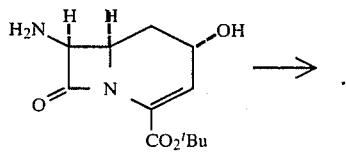

-continued

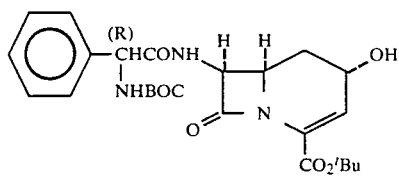

In this Example, 23.8 mg (0.095 m mole) of (R)-N-t-butyloxycarbonylphenylglycine is dissolved in 1 ml of anhydrous tetrahydrofuran, and 0.095 ml (0.095 m mole) of 1N-N-methylmorpholine-tetrahydrofuran and 0.095 ml (0.095 m mole) of 1N-isobutyl chloroformate-tetrahydrofuran are added at a temperature of −30° C. The mixture is stirred for 30 minutes and 20 mg (0.079m mole) of (±)-cis-7β-amino-4α-hydroxy-1-azabicyclo[4,2,0]oct-2-en-8-on-2-carboxylic acid, t-butyl ester obtained as in the method described in Japanese Published Unexamined Patent Application No. 123591/79 in 1 ml of anhydrous methylene chloride is added thereto. The mixture is allowed to react at a temperature of −30° C. for 45 minutes and at 0° C. for 4 hours. The reaction mixture is then diluted with 5 ml of methylene chloride and is washed successively with water, 1N-HCl, 5%-NaHCO₃, water and saturated sodium chloride solution. The washing is dried with anhydrous sodium sulfate and concentrated to obtain 5 mg of a crude acyl-compound. Purification by silica gel chromatography with 5 g of silica gel and a solvent of n-hexane and ethylacetate (15:1) is carried out to obtain 10 mg of the more polar isomer, 8 mg of the less polar isomer and 4 mg of a mixture thereof. Total yield 57%. Properties of the compounds are as follows.

The more polar isomer IR$\nu_{max}^{CHCl_3}$ (cm⁻¹): 3430, 1780, 1725 (sh), 1717, 1697, 1630.

The less polar isomer IR$\nu_{max}^{CHCl_3}$(cm⁻¹): 3430, 1780, 1722(sh), 1715, 1695, 1630.

REFERENCE EXAMPLE 6

Preparation of cis-7β-[(R)-2-phenylglycinamido]-4α-hydroxy-1-azabicyclo[4,2,0]oct-2-en-8-on-2-carboxylic acid

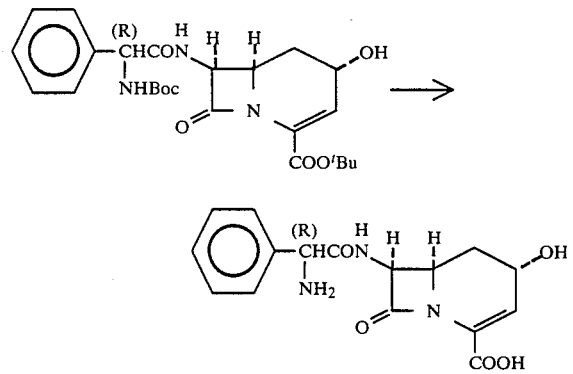

In this Example, 56 mg (0.118 m mole) of the less polar isomer of cis-7β-[(R)-2-t-butyloxycarbonylamino-2-phenylacetamido]-4α-hydroxy-1-azabicyclo[4,2,-0]oct-2-en-8-on-2-carboxylic acid, t-butyl ester obtained as in Reference Example 5 is dissolved in a mixture of 1 ml of anhydrous methylene chloride and 1 ml of anisole, and 2 ml of trifluoroacetic acid is added under ice cooling. The mixture is allowed to stand for 4 hours under ice cooling and then concentrated under reduced pressure. After adding dry benzene, the concentrate is again concentrated to obtain an oily product. The product is triturated with ether and the resulted precipitate is recovered by filtration to obtain 42.1 mg (80%) of a pale yellow powder of the trifluoroacetate of the desired compound. Properties of the product are as follows.

IR$\nu_{max}^{KBr}$(cm⁻¹): 3485, 1780(sh), 1770, 1700(sh), 1685, 1635.

The obtained trifluoroacetate is dissolved in 2 ml of 1M-phosphate buffer (pH 7.0) and subjected to purification using 50 ml of Diaion HP-20AG and a solvent of water to water and methanol (9:1). The purified solution is lyophilized to obtain 28 mg (72%) of the desired compound. Properties of the product are as follows. $[\alpha]_D^{24°} = -26.0°$ (c=0.53, H₂O).

IR$\nu_{max}^{KBr}$(cm⁻¹): 3480, 1780, 1770, 1680–1705, 1570–1650.

NMR (D₂O)δ: 7.52(5H, s), 6.03(1H, d, J=5.4 Hz), 5.5(1H, d, J=5.1 Hz), 5.21(1H, s), 4.28(1H, m), 4.06–3.85(1H, m), 1.76–0.99 (2H, m).

What is claimed is:

1. The optically active compounds of the formula

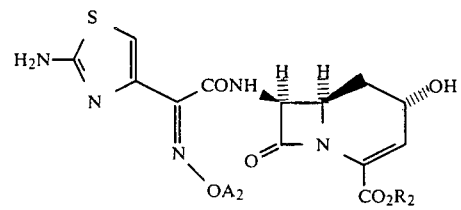

wherein R₂ represents a hydrogen or a group represented by the formula

wherein R₃ is a straight or branched lower alkyl group having 1 to 6 carbon atoms, a straight or branched lower alkoxy group having 1 to 6 carbon atoms or a phenyl group and R₄ is a hydrogen or a straight or branched lower alkyl group having 1 to 6 carbon atoms; and A₂ represents a straight or branched lower alkyl group having 1 to 6 carbon atoms or a straight or branched lower alkyl froup having 1to 6 carbon atoms which is substituted with one or two carboxyl groups, and pharmaceutically acceptable salts thereof.

2. A compound according to claim 1 wherein R₂ is hydrogen.

3. A compound according to claim 1 wherein the OH group is in the form of alpha-bonding.

4. A compound according to claim 1 wherein R₂ is hydrogen, A₂ is a methyl group and the OH group is in the form of alpha-bonding, that is, (4S, 6R, 7S-7-[2-(2-amino-4-thiazolyl)-2-syn-methoxyimino-acetamido]-4-hydroxy-1-azabicyclo[4,2,0]-oct-2-en-8-on-2-carboxylic acid.

5. A compound according to claim 1 wherein R₂ is a hydrogen, A₂ is a 2-carboxypropan-2-yl and the OH group is in the form of alpha-bonding, that is, (4S, 6R, 7S)-7-[2-(2-amino-4-thiazolyl)-2-syn-(2-carboxyprop-2-oxyimino)acetamido]-4-hydroxy-1-azabicyclo[4,2,-0]oct-2-en-8-on-2-carboxylic acid.

* * * * *

UNITED STATES PATENT AND TRADEMARK OFFICE
CERTIFICATE OF CORRECTION

PATENT NO. : 4,663,450

DATED : May 5, 1987

INVENTOR(S) : TADASHI HIRATA, ET AL.

It is certified that error appears in the above-identified patent and that said Letters Patent is hereby corrected as shown below:

AT [57] IN THE ABSTRACT

Lines 5-8, " 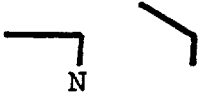 OH " should read - 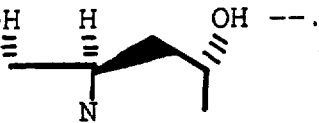 --.

COLUMN 1

Lines 22-24, "  " should read -- 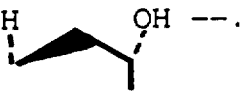 --.

COLUMN 3

Line 5, "162006/78, published" should read --162006/78, 162007/78, published--.

Line 7, "87790/80, 162007/78" should read --87790/80--.

Line 65, "Gra-negative" should read --Gram-negative--.

COLUMN 8

Line 28, "  OH " should read --  --.

Line 56, "mg 0.178" should read --mg (0.178--.

COLUMN 9

Line 36, "(1H,J = 8.4 Hz)," should read --(1H,d,J = 8.4 Hz),--.

UNITED STATES PATENT AND TRADEMARK OFFICE
CERTIFICATE OF CORRECTION

PATENT NO. : 4,663,450

DATED : May 5, 1987

INVENTOR(S) : TADASHI HIRATA, ET AL

It is certified that error appears in the above-identified patent and that said Letters Patent is hereby corrected as shown below:

COLUMN 9

Line 37, "(1H,J = 5.4 Hz)," should read
            --(1H,d,J = 5.4 Hz),--.

COLUMN 11

Line 10-11, 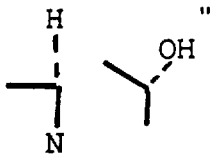 " should read --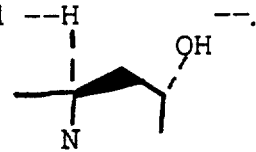--.

COLUMN 12

Line 30, "74 mg of" should read --74 mg (0.356 m mole) of--.

COLUMN 13

Line 4, "MIC (µ/ml)" should read --MIC (µg/ml)--.

COLUMN 18

Line 59, "2-en-8-on-carboxylic" should read
          --2-en-8-on-2-carboxylic--.

UNITED STATES PATENT AND TRADEMARK OFFICE
CERTIFICATE OF CORRECTION

PATENT NO. : 4,663,450

DATED : May 5, 1987

INVENTOR(S) : TADASHI HIRATA, ET AL.

It is certified that error appears in the above-identified patent and that said Letters Patent is hereby corrected as shown below:

COLUMN 20

Line 49, "froup having 1to" should read --group having 1 to--.

Line 58, "7S-7-" should read --7S)-7- --.

Signed and Sealed this

Fifteenth Day of September, 1987

Attest:

DONALD J. QUIGG

Attesting Officer

Commissioner of Patents and Trademarks